United States Patent
Agnatovech et al.

[11] Patent Number: 5,897,582
[45] Date of Patent: Apr. 27, 1999

[54] MIGRAINE RELIEF PRESSURE CAP

[76] Inventors: Stephen Agnatovech; Maria S. Agnatovech, both of 5 Webber St., Wilmington, Mass. 01887

[21] Appl. No.: 08/970,006

[22] Filed: Nov. 13, 1997

[51] Int. Cl.[6] .................................................. A61F 7/00
[52] U.S. Cl. ........................ 607/109; 607/110; 607/112; 607/114
[58] Field of Search .................. 607/108–110, 112, 607/114, 96, 139; 126/204; 62/530

[56] References Cited

U.S. PATENT DOCUMENTS

| | | | |
|---|---|---|---|
| 2,875,447 | 3/1959 | Goldmerstein | 607/109 |
| 2,919,735 | 1/1960 | Prietzsch | 607/109 |
| 2,973,762 | 3/1961 | Koenig | 607/109 |
| 3,159,160 | 12/1964 | Ullom | 607/109 |
| 3,953,892 | 5/1976 | Kennedy et al. | 607/109 |
| 4,382,446 | 5/1983 | Truelock et al. | 607/110 |
| 4,425,917 | 1/1984 | Kuznetz | 607/110 |
| 4,632,104 | 12/1986 | Conrow | 607/110 |
| 4,781,193 | 11/1988 | Pagden | 607/109 |
| 4,832,030 | 5/1989 | De Canto | 607/109 |
| 5,314,456 | 5/1994 | Cohen | 607/109 |
| 5,378,042 | 1/1995 | Danshvar | 607/109 |
| 5,395,400 | 3/1995 | Stafford et al. | 607/109 |
| 5,419,758 | 5/1995 | Vijayan | 607/109 |
| 5,514,170 | 5/1996 | Mauch | 607/109 |

*Primary Examiner*—Robert L. Nasser

[57] ABSTRACT

A migraine reliever is provided including a headband. Further provided is at least one of pressure applicator situated on the head band for effecting the application of pressure to selected points on a head of a user.

1 Claim, 2 Drawing Sheets

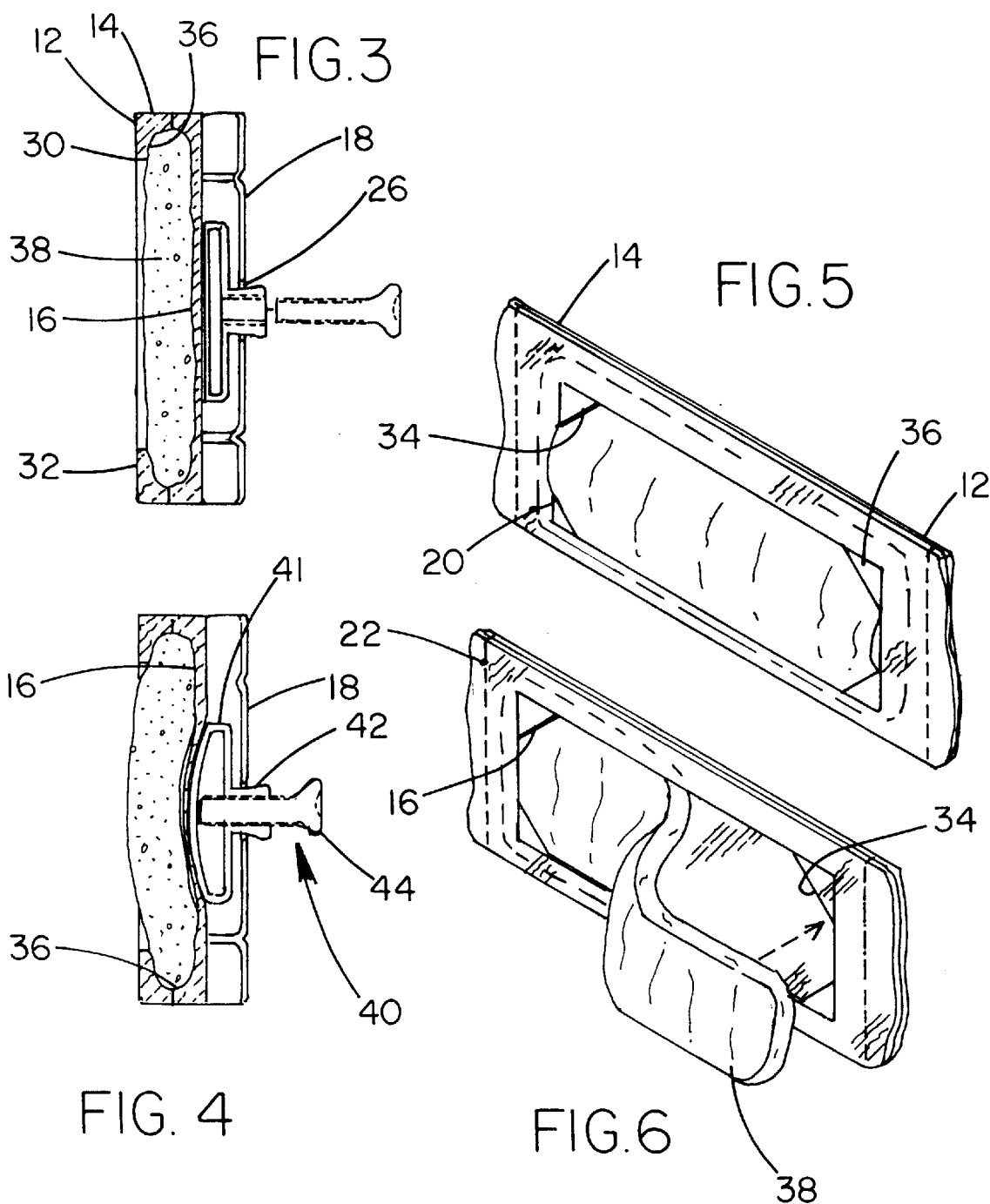

MIGRAINE RELIEF PRESSURE CAP

BACKGROUND OF THE INVENTION

1. Field of the Invention

The present invention relates to head ache relievers and more particularly pertains to a new migraine relief pressure cap for abating the pain associated with migraine headaches.

2. Description of the Prior Art

The use of head ache relievers is known in the prior art. More specifically, head ache relievers heretofore devised and utilized are known to consist basically of familiar, expected and obvious structural configurations, notwithstanding the myriad of designs encompassed by the crowded prior art which have been developed for the fulfillment of countless objectives and requirements.

Known prior art head ache relievers include U.S. Pat. No. 4,781,193; U.S. Pat. No. 4,632,104; U.S. Pat. Des. 347,897; U.S. Pat. No. 5,314,456; U.S. Pat. No. 3,953,892; and U.S. Pat. No. 5,419,758.

In these respects, the migraine relief pressure cap according to the present invention substantially departs from the conventional concepts and designs of the prior art, and in so doing provides an apparatus primarily developed for the purpose of abating the pain associated with migraine headaches.

SUMMARY OF THE INVENTION

In view of the foregoing disadvantages inherent in the known types of head ache relievers now present in the prior art, the present invention provides a new migraine relief pressure cap construction wherein the same can be utilized for abating the pain associated with migraine headaches.

The general purpose of the present invention, which will be described subsequently in greater detail, is to provide a new migraine relief pressure cap apparatus and method which has many of the advantages of the head ache relievers mentioned heretofore and many novel features that result in a new migraine relief pressure cap which is not anticipated, rendered obvious, suggested, or even implied by any of the prior art head ache relievers, either alone or in any combination thereof.

To attain this, the present invention generally comprises a headband with a rectangular strip having a thin closed inner face and an outer face coupled to the inner face thereby defining an interior space. As shown in FIGS. 1 & 2, the interior space is segmented into four discrete compartments via dividers. The outer face of each compartment has a separate elongated horizontal slot formed therein. FIG. 1 shows the headband including a pair of straps each with ends coupled to a top edge of the strip. The straps are oriented at a right angle and form a dome for encompassing a top of a head of a user. The inner face has an upper lip and a lower lip extending inwardly along a length thereof. Further, each divider has a pair of opposite inwardly extending lips formed thereon between the corresponding upper and lower lip. Each lip has an L-shaped cross-section to define a peripheral slot behind each compartment. Next provided is a plurality of flexible cold packs each having a rectangular configuration. Each cold pack has a front face, rear face, and a periphery formed therebetween. As shown in FIGS. 5 & 6, each flexible cold pack is removably situated within the slot of an associated one of the compartments. FIGS. 3 & 4 shows a plurality of pressure applicators each including a flexible hollow disk situated within the interior space of the corresponding compartment. The disk has an outboard face with an aperture formed therein. A threaded sleeve is integrally coupled about the apertures and extends therefrom. Each pressure applicator further includes a screw having a first threaded end and a second end with a knob integrally formed thereon. During use, the first threaded end is screwably coupled to the threaded sleeve with the knob extending from the corresponding slot. Each disk may be slid freely between ends of the interior space of the associated compartment. Further, the screw may be tightened such that an inboard face of the disk protrudes. Such protruding affect effects the bulging of the cold pack at a discrete point. As such, when worn, the head band may be used to apply pressure to and reduce the temperature of selected points on a head of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore,. that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new migraine relief pressure cap apparatus and method which has many of the advantages of the head ache relievers mentioned heretofore and many novel features that result in a new migraine relief pressure cap which is not anticipated, rendered obvious, suggested, or even implied by any of the prior art head ache relievers, either alone or in any combination thereof.

It is another object of the present invention to provide a new migraine relief pressure cap which may be easily and efficiently manufactured and marketed.

It is a further object of the present invention to provide a new migraine relief pressure cap which is of a durable and reliable construction.

An even further object of the present invention is to provide a new migraine relief pressure cap which is susceptible of a low cost of manufacture with regard to both materials and labor, and which accordingly is then susceptible of low prices of sale to the consuming public, thereby making such migraine relief pressure cap economically available to the buying public.

Still yet another object of the present invention is to provide a new migraine relief pressure cap which provides in the apparatuses and methods of the prior art some of the advantages thereof, while simultaneously overcoming some of the disadvantages normally associated therewith.

Still another object of the present invention is to provide a new migraine relief pressure cap for abating the pain associated with migraine headaches.

Even still another object of the present invention is to provide a new migraine relief pressure cap that includes a headband. Further provided is at least one of pressure applicator situated on the head band for effecting the application of pressure to selected points on a head of a user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view of the head band of the present invention taken along line 3—3 shown in FIG. 2.

FIG. 4 is a cross-sectional view of the head band of the present invention with the screw engaged with the disk.

FIG. 5 is a perspective view of a cold pack of the present invention situated within one of the compartments of the head band.

FIG. 6 is a perspective view of a cold pack of the present invention in a partially removed orientation.

DESCRIPTION OF THE PREFERRED EMBODIMENT

Figure 1:
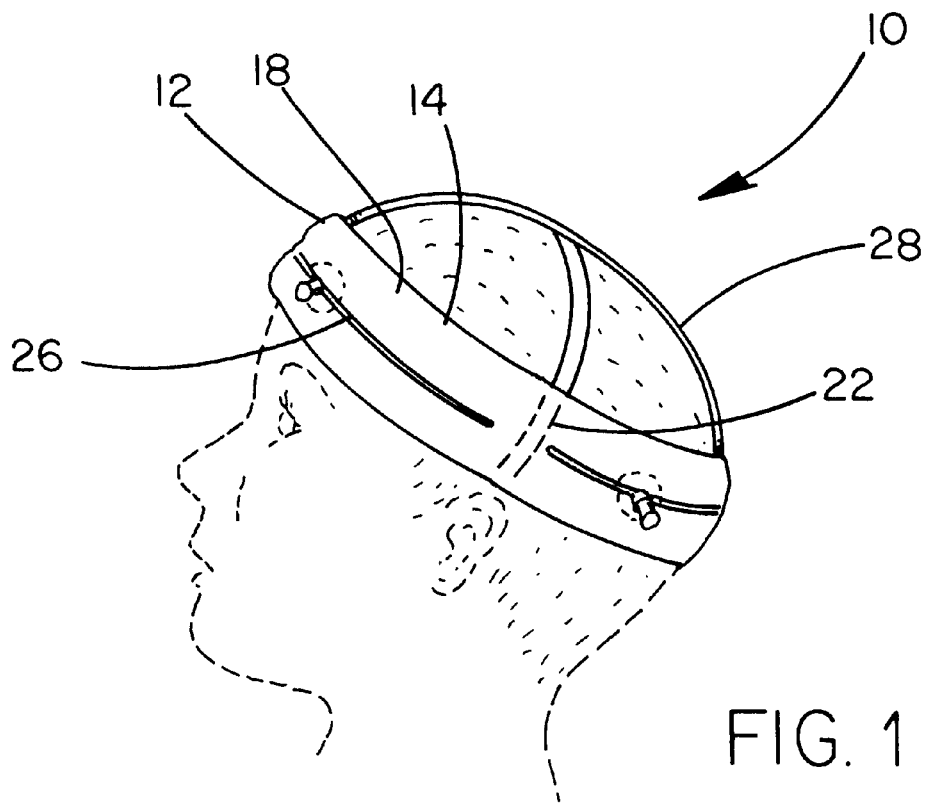
FIG. 1 is a perspective of a new migraine relief pressure cap according to the present invention.

With reference now to the drawings, and in particular to FIGS. 1 through 6 thereof, a new migraine relief pressure cap embodying the principles and concepts of the present invention and generally designated by the reference numeral 10 will be described.

Figure 2:
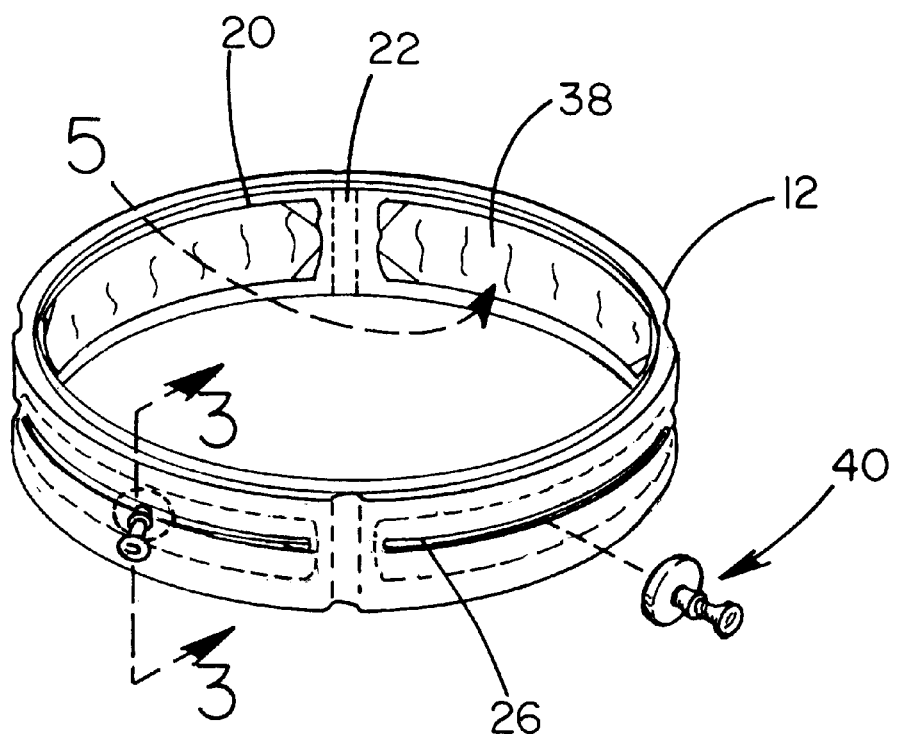
FIG. 2 is a perspective view of the present invention.

The present invention, as designated as numeral 10, includes a headband 12 with a closed-loop rectangular strip 14 having a thin closed inner face 16 and a more rigid outer face 18 coupled to the inner face thereby defining an interior space. The inner face is preferably lined with felt. As shown in FIGS. 1 & 2, the interior space is segmented into four discrete compartments 20 via dividers 22. Preferably, four vertical dividers are provided to define four quadrants. One of the dividers is preferably situated at a center of the forehead when the head band is worn for reasons that will become apparent. As an option, the rectangular strip is spilt with a pair of pile fasteners situated at ends thereof for permitting a secure fit on the head of the user.

The outer face of each compartment has a separate elongated horizontal slot 26 formed therein and extending between the associated dividers. FIG. 1 shows the headband including a pair of straps 28 each with ends coupled to a top edge of the strip. The straps are oriented at a right angle and form a dome for encompassing a top of a head of a user. The straps are flexible in the preferred embodiment.

The inner face of the head band has an upper lip 30 and a lower lip 32 extending inwardly along a length thereof. Further, each divider has a pair of opposite inwardly extending lips 34 formed thereon between the corresponding upper and lower lips. Each lip has an L-shaped cross-section to define a peripheral slot 36 behind each compartment. The lips preferably extend no further than ⅛ inch toward the center of the head band.

Next provided is a plurality of flexible viscous liquid-filled cold packs 38 each having a rectangular configuration. Each cold pack has a front face, rear face, and a periphery formed therebetween. As shown in FIGS. 5 & 6, each flexible cold pack is removably situated within the slot of an associated one of the compartments. When removed, the cold packs are adapted to be frozen for future use.

FIGS. 3 & 4 shows a plurality of pressure applicators 40 each including a flexible hollow disk 41 situated within the interior space of the corresponding compartment. The disk has an outboard face with an aperture formed therein. A threaded sleeve 42 is integrally coupled about the apertures and extends therefrom. Each pressure applicator further includes a screw 44 having a first threaded end and a second end with a knob integrally formed thereon.

During use, the first threaded end is screwably coupled to the threaded sleeve with the knob extending from the corresponding slot. Each disk may be slid freely between ends of the interior space of the associated compartment. Further, the screw may be tightened such that an inboard face of the disk protrudes. Such protruding affect effects the bulging of the cold pack at a discrete point. As such, when worn, the head band may be used to apply pressure to and reduce the temperature of selected points on a head of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A migraine reliever comprising, in combination:
   a headband including a rectangular strip having a thin closed inner face lined with felt and an outer face coupled to the inner face thereby defining an interior space, the interior space being segmented into four discrete compartments via dividers, wherein the headband is split with a pair of pile fasteners situated at ends thereof, the outer face of each compartment having an elongated horizontal slot formed therein, the headband including a pair of flexible straps each having ends coupled to a top edge of the strip such that the straps are oriented at a right angle and form a dome, the inner face having an upper lip and a lower lip extending inwardly along a length thereof and each divider having a pair of opposite inwardly extending lips formed thereon, each lip having an L-shaped cross-section to define a peripheral slot behind each compartment, wherein the lips extend no further than $\frac{1}{8}$ of an inch toward a center of the headband;

a plurality of flexible liquid filled cold packs each having a rectangular configuration with a front face, rear face, and a periphery formed therebetween, each flexible cold pack situated within the slot of one of the compartments;

a plurality of pressure applicators each including a flexible hollow disk situated within the interior space of one of the compartments, the disk having an outboard face with an aperture formed therein and a threaded sleeve integrally coupled thereto and extending therefrom, each pressure applicator further including a screw having a first threaded end and a second end with a knob integrally formed thereon with the first threaded end screwably coupled to the threaded sleeve, whereby each disk may be slid freely between ends of the interior space of one of the compartments and the screw tightened such that an inboard face of the disk protrudes thereby effecting a bulging of the cold pack at a discrete point such that when worn, the headband may be used to apply pressure to and reduce a temperature of selected points on a head of the user.

* * * * *